United States Patent
Bak et al.

(10) Patent No.: US 10,818,051 B2
(45) Date of Patent: Oct. 27, 2020

(54) RELATIVE SIGNATURE TRAITS OF COHORTS

(71) Applicant: International Business Machines Corporation, Armonk, NY (US)

(72) Inventors: Peter Bak, Yokneam Ilit (IL); Swapnil Chhabra, Arlington Heights, IL (US); Joern Jaskolowski, Copenhagen (DK); Adam Perer, Pittsburgh, PA (US); Avi Yaeli, Ramot Menashe (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/214,160

(22) Filed: Dec. 10, 2018

(65) Prior Publication Data

US 2020/0184691 A1    Jun. 11, 2020

(51) Int. Cl.
*G06T 11/20*    (2006.01)
*G06F 16/901*    (2019.01)

(52) U.S. Cl.
CPC ........ *G06T 11/206* (2013.01); *G06F 16/9024* (2019.01)

(58) Field of Classification Search
None
See application file for complete search history.

(56) References Cited

U.S. PATENT DOCUMENTS

| 9,430,616 B2 | 8/2016 | Duftler et al. |
| 2014/0058738 A1 | 2/2014 | Yeskel |
| 2014/0257045 A1 | 9/2014 | Hu et al. |
| 2015/0261914 A1* | 9/2015 | Kapushesky ....... G06F 16/1794 707/634 |
| 2015/0324090 A1 | 11/2015 | Kostirev et al. |
| 2017/0139991 A1* | 5/2017 | Teletia ................ G06F 16/9024 |

OTHER PUBLICATIONS

Rahul C. Basole et al., "A visual analytics approach to understanding care process variation and conformance", Proc 2015 Workshop Vis Anal Healthc, 2015.

Adam Perer et al., "Mining and exploring care pathways from electronic medical records with visual analytics", Journal of Biomedical Informatics, vol. 56, Aug. 2015, pp. 369-378.

(Continued)

*Primary Examiner* — Yanna Wu
(74) *Attorney, Agent, or Firm* — Ziv Glazberg (57) ABSTRACT

A pathway for each entity in a cohort may be extracted from raw data comprising a plurality of events. A common graph structure may be created based the extracted pathways. For each cohort, a relative signature trait may be computed for each edge based on a number of appearances of the edge in the extracted pathways that are associated with the cohort. A relationship expression may be obtained. The relationship expression may be with respect to at least two cohorts for which relative signature traits were computed. The common graph structure may be processed based on the relationship expression to determine an output label for each edge. A visualization of the common graph structure may be displayed.

18 Claims, 6 Drawing Sheets

(56) References Cited

OTHER PUBLICATIONS

"Ayasdi Clinical Variation Manager", www.ayasdi.com, product brief. Available at: https://s3.amazonaws.com/cdn.ayasdi.com/wp-content/uploads/2017/08/03175923/AYASDI-Ayasdi-Clinical-Variation-Manager-PB-053017v01.pdf (retrieved Nov. 25, 18).

Yiye Zhang et al., "Paving the COWpath: Learning and visualizing clinical pathways from electronic health record data", Journal of Biomedical Informatics, Dec. 2015, vol. 58, pp. 186-197.

Takanori Yamashita et al., "Visualization of key factor relation in clinical pathway", Procedia Computer Science, 2015, vol. 60, pp. 342-351.

Jessica Pinaire et al., "Patient healthcare trajectory. An essential monitoring tool: a systematic review", Health Information Science and Systems, Dec. 2017.

Azadeh Nikfarjam et al., "Towards generating a patient's timeline: Extracting temporal relationships from clinical notes", Journal of Biomedical Informatics, Dec. 2013, vol. 46, Supplement, pp. S40-S47.

Zitao Liu et al., "Clinical time series prediction: towards a hierarchical dynamical system framework", Artificial Intelligence in Medicine, Sep. 2015, vol. 65, Issue 1, pp. 5-18.

Elias Egho et al., "An approach for mining care trajectories for chronic diseases", 2013, 14th Conference on Artificial Intelligence in Medicine, May 2013, Murcia, Spain, Springer.

\* cited by examiner

| Group | Link | Support | High | Med | Low |
|---|---|---|---|---|---|
| Cohort1 | D1→T2 | 1244 | yes | no | no |
| Cohort1 | D1→T3 | 302 | no | yes | no |
| Cohort1 | D1→T4 | 24 | no | no | yes |
| Cohort1 | T2→O5 | 800 | yes | no | no |
| Cohort1 | T3→O5 | 134 | no | yes | no |
| Cohort1 | T2→O6 | 145 | no | yes | no |
| Cohort1 | T4→O6 | 20 | no | no | yes |
| Cohort2 | D1→T2 | 543 | no | yes | no |
| Cohort2 | D1→T3 | 76 | no | no | yes |
| Cohort2 | D1→T4 | 637 | no | yes | no |
| Cohort2 | T2→O5 | 34 | no | yes | no |
| Cohort2 | T3→O5 | 34 | no | yes | no |
| Cohort2 | T2→O6 | 2 | no | no | yes |
| Cohort2 | T4→O6 | 30 | no | yes | no |
| Cohort3 | D1→T2 | 200 | no | yes | no |
| Cohort3 | D1→T3 | 156 | no | yes | no |
| Cohort3 | D1→T4 | 10 | no | no | yes |
| Cohort3 | T2→O5 | 10 | no | yes | no |
| Cohort3 | T3→O5 | 3 | no | yes | yes |
| Cohort3 | T2→O6 | 30 | yes | no | no |
| Cohort3 | T4→O6 | 1 | no | no | yes |

RELATIVE SIGNATURE TRAITS OF COHORTS

TECHNICAL FIELD

The present disclosure relates to data analysis in general, and to, big data analysis in particular.

BACKGROUND

Big data analysis is the analysis of large volumes of data that may be too large or complex for traditional data-processing application software to adequately deal with. The analysis and visualization of such large data set may be important challenges to overcome.

Today, data recorded in healthcare systems amounts to large volumes. Each treatment the patient is given may be recorded. Each procedure the patient undergoes is monitored. Lab results are available in electronic manner, as well as the diagnosis of the healthcare professionals. In some cases, outcomes, such as hospitalization or death, may also be recorded. Such big data may be used for research purposes.

BRIEF SUMMARY

One exemplary embodiment of the disclosed subject matter is a method comprising: for each entity in each cohort, extracting a pathway for the each entity, wherein the pathway is extracted from raw data comprising a plurality of events, wherein the pathway is extracted based on events of interest in the plurality of events; creating a common graph structure based the extracted pathways, wherein the common graph structure comprising nodes and edges; for each cohort, computing a relative signature trait for each edge, wherein said computing is based on a number of appearances of the each edge in the extracted pathways that are associated with the each cohort; obtaining a relationship expression with respect to at least two cohorts, wherein each of the at least two cohorts having a relative signature trait computed in said computing; processing the common graph structure based on the relationship expression to determine an output label for each edge; and displaying a visualization of the common graph structure, wherein the visualization comprises a visual cue indicative of the output label of each edge.

Another exemplary embodiment of the disclosed subject matter is a non-transitory computer readable medium retaining program instructions, which program instructions when read by a processor, cause the processor to perform: for each entity in each cohort, extracting a pathway for the each entity, wherein the pathway is extracted from raw data comprising a plurality of events, wherein the pathway is extracted based on events of interest in the plurality of events; creating a common graph structure based the extracted pathways, wherein the common graph structure comprising nodes and edges; for each cohort, computing a relative signature trait for each edge, wherein said computing is based on a number of appearances of the each edge in the extracted pathways that are associated with the each cohort; obtaining a relationship expression with respect to at least two cohorts, wherein each of the at least two cohorts having a relative signature trait computed in said computing; processing the common graph structure based on the relationship expression to determine an output label for each edge; and displaying a visualization of the common graph structure, wherein the visualization comprises a visual cue indicative of the output label of each edge.

Yet another exemplary embodiment of the disclosed subject matter is an apparatus comprising a processor and memory, wherein the processor is configured to perform: for each entity in each cohort, extracting a pathway for the each entity, wherein the pathway is extracted from raw data comprising a plurality of events, wherein the pathway is extracted based on events of interest in the plurality of events; creating a common graph structure based the extracted pathways, wherein the common graph structure comprising nodes and edges; for each cohort, computing a relative signature trait for each edge, wherein said computing is based on a number of appearances of the each edge in the extracted pathways that are associated with the each cohort; obtaining a relationship expression with respect to at least two cohorts, wherein each of the at least two cohorts having a relative signature trait computed in said computing; processing the common graph structure based on the relationship expression to determine an output label for each edge; and displaying a visualization of the common graph structure, wherein the visualization comprises a visual cue indicative of the output label of each edge; and wherein said memory is configured to retain the relative signature traits, the common graph structure and the output labels.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

The data recorded in healthcare systems provides Real World Evidence (RWE) to the actual clinical pathways that patients undergo during complex care processes in Healthcare. For example, how doctors in practice treat Congestive Heart Failure (CHF) patients based on existing patient conditions, past treatments, comorbidities, provider's preferences and treatment options.

Comparing pathways of different cohorts of patients may be essential to address clinical research questions, understanding drug treatments for life science companies as well as to compare the quality, cost and outcome of different healthcare facilities for providers. Examples of questions that may be answered by such data may be: how do pathways in facility A differ than facility B? What is common across all our facilities and where is the variability? How do treatment pathways of different schizophrenia cluster groups compare?

A nave approach to comparing clinical pathways may be to summarize somehow the pathways of each group of patients and then visually compare the results. However, summarization of pathways leads to unique graph structure and layout for every group that makes the task of understanding and comparison on real data cohorts practically impossible.

Mining pathways of individuals and groups is a challenging area. The data model of individual pathways may be a trajectory of all possible medical/clinical states and healthcare decisions. The data may be high dimensional, thus even summarizing two trajectories of two patients may become a challenging task, let alone the ability to summarize and compare pathways of thousands of patients belonging to different groups within or across cohorts.

One technical solution provided by the disclosed subject matter may be to build a common graph structure on which clinical pathways can be projected and compared in a consistent manner. In some exemplary embodiments, a signature trait for each individual cohort group in the common graph may be computed, such as based on frequencies of pathways of the cohort. Relative signature traits may be computed, such as by binning group frequencies into signature trait categories. The categories may be, for example, frequency categories, dominance categories, or the like.

In some exemplary embodiments, the relative signature traits may be computed and re-used for different processing and different relationship expressions, representing different groups of entities from the cohorts. In some exemplary embodiments, in each such processing, different output labels may be determined for each edge of the common graph structure without re-creating the graph and without additional pre-processing. In some cases, the processing of the expression is performed without re-iterating over the entities themselves. It is noted that a nave solution would utilize the relationship expression to determine a set of entities which it covers and then analyze that group. However, the disclosed subject matter avoids such processing and instead utilizes the relative signature traits of the relevant cohorts. In some exemplary embodiments, the processing of each relationship expression is performed without computing traits based on pathways that are associated with the entities represented by the group expressed by the relationship expressions.

In some exemplary embodiments, visualization may be displayed to the user in a manner that the user can comprehend, albeit the large volume of data that is analyzed and the large number of variations represented by each cohort.

In some exemplary embodiments, visualization may be a visualization of a relationship of two or more cohorts, such as visualizing patients in one cohort but not in the other, patients in one of two cohorts, patients that members of two or more cohorts, or the like.

In some exemplary embodiments, visualization may be achieved by using a Sankey diagram, or using other visualization methods. In some exemplary embodiments, each group may be displayed individually in small multiples. Additionally or alternatively, the comparison results may be displayed on a single graph, such as by showing a unique pathway that is representative of the difference between the cohorts. Additionally or alternatively, visual mapping may be used to color code relative signature traits. In some exemplary embodiments, the color code may be used to highlight commonalities or differences between cohorts. Additionally or alternatively, the layout of the graph may be simplified to combine pathway nodes-links with similar signature trait relationships between the groups being compared. Additionally or alternatively, the layout may be simplified by removing from the common graph structure nodes/links below a certain threshold.

One technical effect may be to provide a visualization of big data information that can be comprehended by a person, without having to review the data set itself. The disclosed subject matter may address the problem of efficiency of using an electronic device for reviewing big data associated with cohorts. The problem may be specifically acute where the information to be presented is in large volume and the display is relatively small. The disclosed subject matter may enable a user to quickly access relevant data to user queries. Furthermore, the disclosed subject matter may provide non-conventional display visualizations of cohort-related data, and in particular regarding comparative cohort-related data.

In some exemplary embodiments, the disclosed subject matter may provide for performance improvement. Instead of computing for each query data on its own, initial pre-processing may be performed, and the comparative analysis may be performed without having to re-process the entire data set. Instead, the comparative analysis is performed efficiently using the relative signature traits of the cohorts.

The disclosed subject matter may provide for one or more technical improvements over any pre-existing technique and any technique that has previously become routine or conventional in the art. Additional technical problem, solution and effects may be apparent to a person of ordinary skill in the art in view of the present disclosure.

Figure 1:
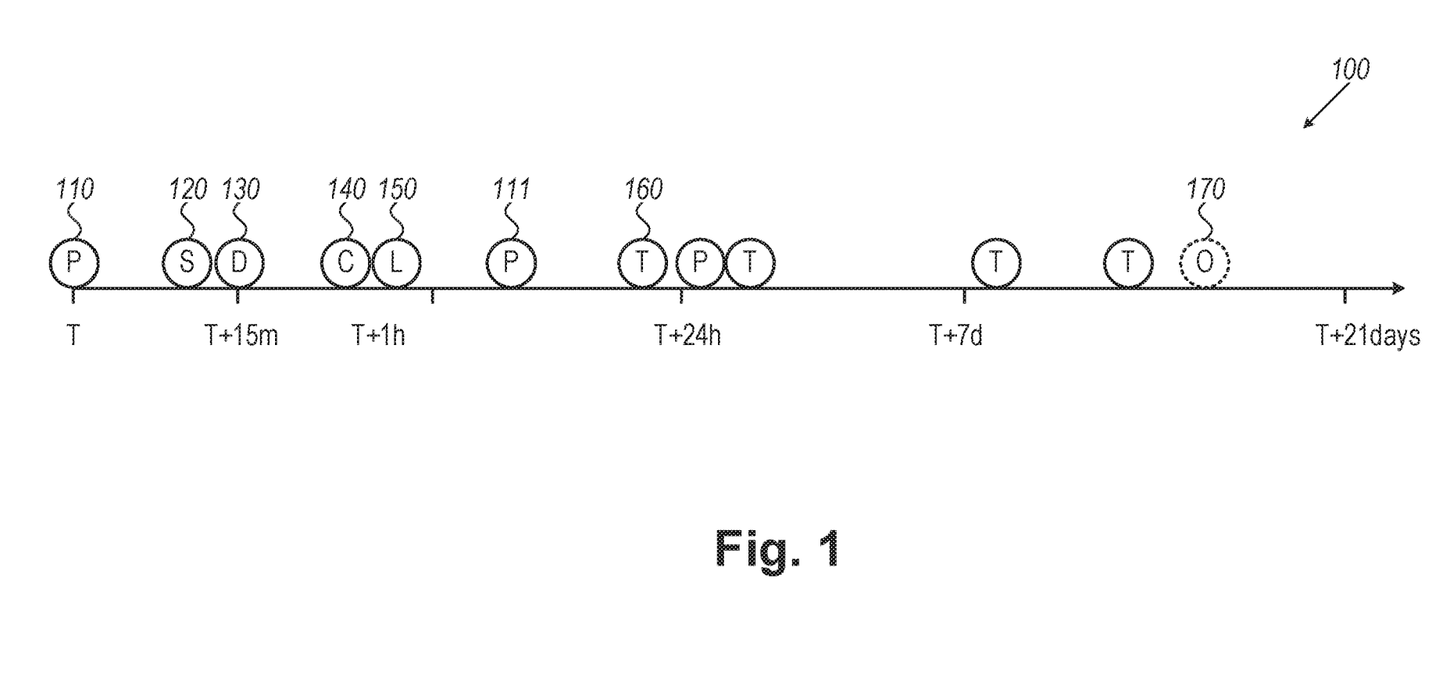
FIG. 1 shows an illustration of a clinical pathway of a patient, in accordance with some exemplary embodiments of the disclosed subject matter.

Referring now to FIG. 1 illustrating a clinical pathway of a patient, in accordance with some exemplary embodiments of the disclosed subject matter.

Pathway 100 illustrates events over time relating to a patient. The events may be obtained based on RWE, such as aggregated from data repositories relating to lab tests, medical records, insurance, or the like. Pathway 100 indicates different events such as Procedure 110 (e.g., medical procedure), Score 120 (e.g., CT results, diagnosis scores, or the like), Diagnosis 130 (e.g., doctor's diagnosis of medical condition), Condition 140 (e.g., bleeding, infection, or the like), Lab Results 150, Treatment 160 (e.g., prescribed drugs, physical therapy, or the like), Outcome 170 (e.g., hospitalization, death, cured or the like), or the like.

It is noted that each event occurs at a time. The time may be normalized to a base event. For example, in CHF, the base event may be the time at which the heart failure occurred. Additionally or alternatively, the base event may be Procedure 110 which represents a lifesaving surgery the patient underwent. In some exemplary embodiments, the event time may be relative to the time of the base event (e.g., T+1 h indicating one hour after the base event; T+7 d indicating a week after the base event; or the like).

As can be appreciated, each patient may be associated with a large volume of events. The patient may be associated with events of different types and with different events of the same type (e.g., Procedure 110 and Procedure 111).

Figure 2:
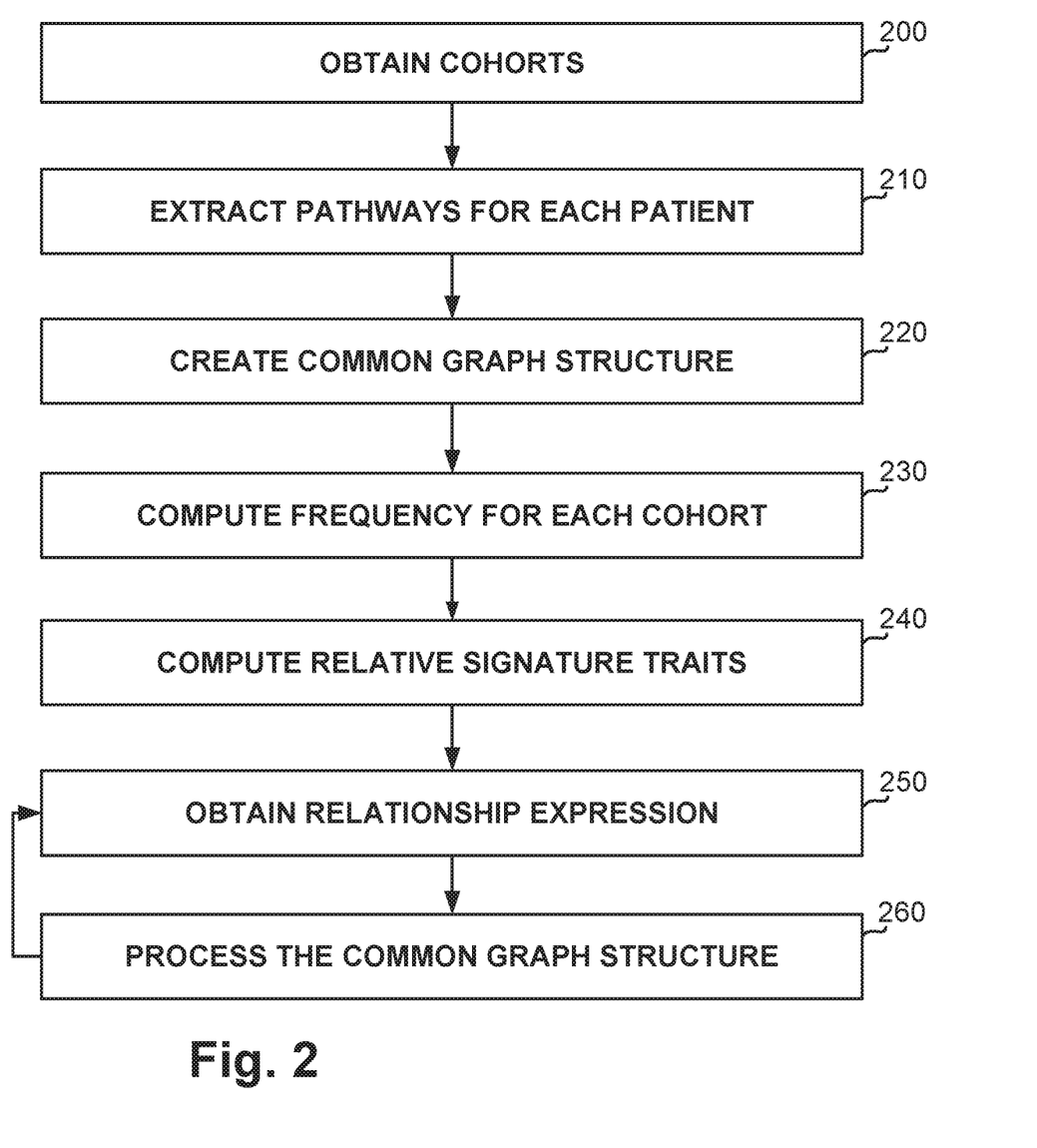
FIG. 2 shows a flowchart diagram of a method, in accordance with some exemplary embodiments of the disclosed subject matter.

Referring now to FIG. 2 showing a flowchart diagram of a method, in accordance with some exemplary embodiments of the disclosed subject matter.

On Step 200, datasets representing the cohorts may be obtained. A cohort may represent a group of individuals having a common characteristic, such as common ethnicity, gender, age group, geographic location, medical care professional, or the like. In some exemplary embodiments, the dataset may be obtained from database comprising clinical or medical events for patients. A set of cohorts may be defined, such as implicitly or explicitly. In some exemplary embodiments, implicit definition may be provided by indicating the common characteristic. Each patient may be compared to the common characteristic to determine whether or not that characteristic is exhibited in the patient. A cohort may include all patients that exhibit the characteristic. Additionally or alternatively, explicit definition may include a list of patients that form the cohort. It is noted that the same patient may be a member of zero, one, two or more cohorts. The cohorts are hereinbelow denoted as $C_1$, $C_2$, $C_3$ and so forth.

On Step 210, for each patient that is a member of any of the cohorts, a pathway of the patient may be extracted. The pathway may be a set of events associated with the subject patient. In some exemplary embodiments, a user may define a list of events of interest (EoI). The EoIs may be milestones events, events relating to an hypothesis a researcher is examining, or the like. For example, in CHF, blood drawing procedure may be considered as a non EoI, while surgery may be considered EoI.

In some exemplary embodiments, the pathway may be an ordered list of events, where the order of the nodes is based on the time. In some cases, the time may be retained explicitly. In other embodiments, the time may be indicated implicitly by the order, such that if between two events one hour had passed or one day had passed, and assuming in between the two events, no other EoI occurred, then the two events would follow each other and appear the same regardless of the time elapsed in between.

On Step 220, a common graph structure may be created. The graph may comprise nodes representing the states of the pathways extracted on Step 210. Edges between the nodes may be added based on the pathways. For example, the edge between S1 and S2 may indicate that there is a pathway that includes a transition from the first state to the second state.

On Step 230, for each cohort, a cohort frequency may be computed on each edge of the common graph structure of Step 220. The frequency may be an average number of times the transition exists in pathways of the cohort within a time period. Additionally or alternatively, the frequency may be an average number of times the transition is exhibited in the cohort within a time period (e.g., counted more than once per pathway, depending on the actual number of occurrences per pathway). Additionally or alternatively, the frequency may be computed as a proportion of the number of times the transition is exhibited in the cohort with respect to the total number of transitions. Additionally or alternatively, a support may be computed instead of the frequency, indicating an overall number of pathways exhibiting the transition or overall number of times the transition is exhibited in the cohort. In some exemplary embodiments, the support may or may not be normalized.

Figure 3:
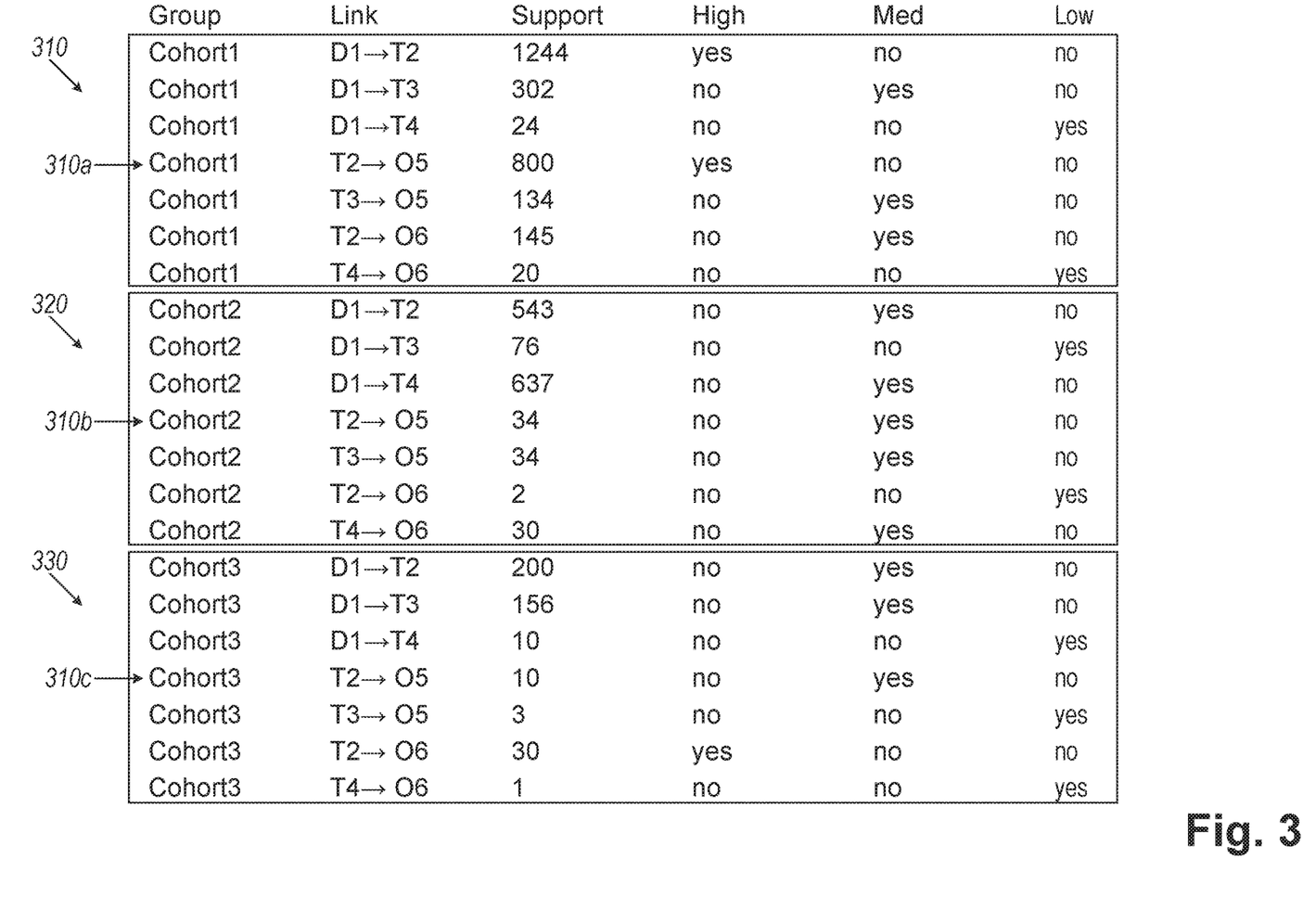
FIG. 3 illustrates a table showing cohort analysis, in accordance with the disclosed subject matter.

Referring to FIG. 3, illustrating a table showing cohort analysis, in accordance with the disclosed subject matter.

The table of FIG. 3 represents information regarding the following illustrative example. There are three groups of CHF patients: Cohort1, Cohort2 and Cohort3, which differ in their insurance plan. In this example there are six types of EoIs, denoted XN, where X is the type of EoI and N is the serial number of the EoI. The type of EoI may is D for a diagnosis event, T for a treatment event and O for an outcome event. The events are as follows: D1—first diagnosis event of Congestive Heart Failure (CHF), T2—Treatment with Beta Blockers, T3—Treatment with Diuretics, T4—Treatment with Antihypertensive, O5—Hospitalization, O6—Death. D1 may be the base event of this example.

The table illustrates information regarding three cohorts, indicated as Cohort1 310, Cohort2 320, and Cohort3 330. Each edge in the common graph structure is represented by a different row, and a support metric is indicated. For example, Row 310a represented the edge between T2 and O5 (i.e., treatment with beta blockers that was followed by hospitalization), which appears 800 times in Cohort1. In Rows 310b and 310c, it can be seen that the same edge has support of 34 in Cohort2 and 10 in Cohort3.

On Step 240, relative signature traits may be computed. In some exemplary embodiments, for each cohort, a relative signature trait may be computed by binning group frequencies or supports into categories. For example, the categories may indicate a range of support/frequency values. As another example, the categories may represent dominance categories. In some exemplary embodiments, sub-paths that share a common signature trait may be treated together as a single edge. The unified treatment may be with respect to analysis of the data, such as to extract insights from the big data. Additionally or alternatively, the unified treatment may be with respect to display and visualization. In some cases, a unified representation may be displayed, and the user may interact with the unified representation to receive a detailed display of the detailed information. Hence, providing for an efficient user interface, useful in particular for electronic devices having limited-sized display.

In the present illustrated example, the relative signature traits are labels of high, medium and low, where each label is provided to a corresponding third of the population—the upper third, the middle third and the lower third. In other embodiments, other categorizations may be used, such as, for example, percentile-based categorizations. Referring again to FIG. 3, Row 310a is labeled with high relative signature trait, while in Rows 310b, 310c of the other cohorts, the same edge is labeled with medium relative signature trait.

On Step 250, a relationship expression may be obtained. The relationship expression may be provided by a user. In some exemplary embodiments, the expression may be provided in terms of set theory or using set algebra. The expression may indicate which group of patients is being examined. For example, the expression may be $C_1 \cup C_2 \cup C_3$, representing patients of either cohorts. As another example, the expression may be $C_1 \cap C_2 \cap C_3$, representing patients in all cohorts. As yet another example, the expression may be $(C_1 \cap \neg C_2) \cup (C_2 \cap \neg C_1)$, representing patients that are either members of Cohort1 or of Cohort2 but not of both.

On Step 260, the common graph structure may be analyzed with respect to the relationship expression. Instead of determining the list of patients that are included in the group according to the expression, the relative traits may be utilized to represent a representative patient of each cohort. The traits are then used to process the data and infer insights or to provide a visualization to be displayed to the user. The visualization may emphasize the traits that are unique for the processed group rather than the other cohorts. The processing may require a substantial reduced amount of processing power in comparison to processing the entire group. Furthermore, the processing may provide useful insights to the unique traits of the group, which may be used to compare that group to the other cohorts.

In some exemplary embodiments, the processing may provide an output label for each edge. The output label may represent an insight relating to the edge and based on the cohorts. The output label may indicate, for example, the relative signature trait of the group represented by the expression. Additionally, or alternatively, the output label may indicate whether the relative signature trait is unique to one cohort or not. The output label may be provided to the user, such as in a visualized manner, using colors, patterns, or the like. Additionally, or alternatively, the output label may be the basis for processing the cohort information, such as to infer insights therefrom.

In some exemplary embodiments, visualization can be used to highlight the comparison function. For example, one may provide a visualization for $C_1-(C_2 \cup C_3)$ to highlight the traits that are different between C1 and both C2 and C3. Additionally or alternatively, if a cohort has a relative signature trait that is different than all other cohorts, such information may be of importance and useful to derive insights as to the differentiation factors between the cohorts.

In some exemplary embodiments, the visualization may group sub-paths that consist of edges that have the same properties together. A sub-path may be represented by a single aggregative edge in a visualization. In some exemplary embodiments, in a user interface, the user may instruct the user interface to fold or collapse the sub-path. For example, the user may click on, hover above, or otherwise interact with the aggregative edge to cause the user interface to collapse the sub-path and show the edges comprised thereby individually. In some exemplary embodiments, the user may thereafter click, hover or otherwise interact with an edge of the sub-path to fold the sub-path to be shown as a single aggregative edge once more.

In some exemplary embodiments, if another query is desired, a new relationship expression may be obtained in Step 250, and the common graph structure may be re-processed accordingly in Step 260. The common graph structure may not be recalculated, and the relative signature traits may be maintained. Hence, reducing computation resources required for performing multiple different analyses of the cohorts.

Figure 4A:
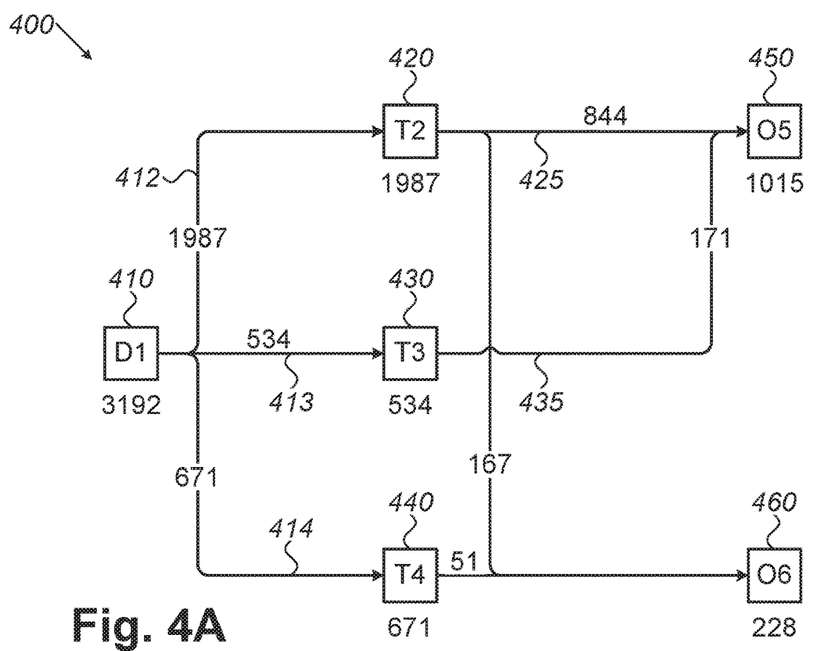
FIG. 4A shows an illustration of a common graph structure, in accordance with some exemplary embodiments of the disclosed subject matter.

Referring now to FIG. 4A showing an illustration of a common graph structure, in accordance with some exemplary embodiments of the disclosed subject matter.

Graph 400 comprises nodes and edges. Each node, such as Nodes D1 410, T2 420, T3 430, T4 440, O5 450, O6 460 may represent a different EoI. An edge between two nodes represents an order of appearance in a pathway. For example, Edge 412 represents that in at least one pathway, the event of D1 410 (first diagnosis event of CHF) is followed by the event of T2 420 (treatment with beta blockers), without any other EoI in between.

The weights indicated on the edges represent the overall support of such edge in the pathways. For example, there are 1987 cases where event D1 410 is followed by event T2 420, as indicated by Edge 412.

The weights indicated on the nodes indicate the number of supports for the event itself. For example, Event D1 is found 3192 times. Out of those, 1987 times the next EoI was T2 420, as indicated by Edge 412, 534 times the next EoI was T3 430 as indicated by Edge 413, and 671 times the next EoI was T4 440, as indicated by Edge 414. Similarly, the 1015 times O5 450 was observed is split between 844 times, when T2 420 preceded it, as indicated by Edge 425 and 171 times, when T3 430 preceded it, as indicated by Edge 435. From an absence of an edge between T4 440 and O5 450, it is indicated that in no case was a treatment with antihypertensive was followed by hospitalization. It is also noted that only in 51 cases there is a successive outcome of death (O6 460). The remaining cases, ended without any outcome either because the outcome has yet to occur or because the patient may have healed and no outcome was recorded.

Figure 4B:
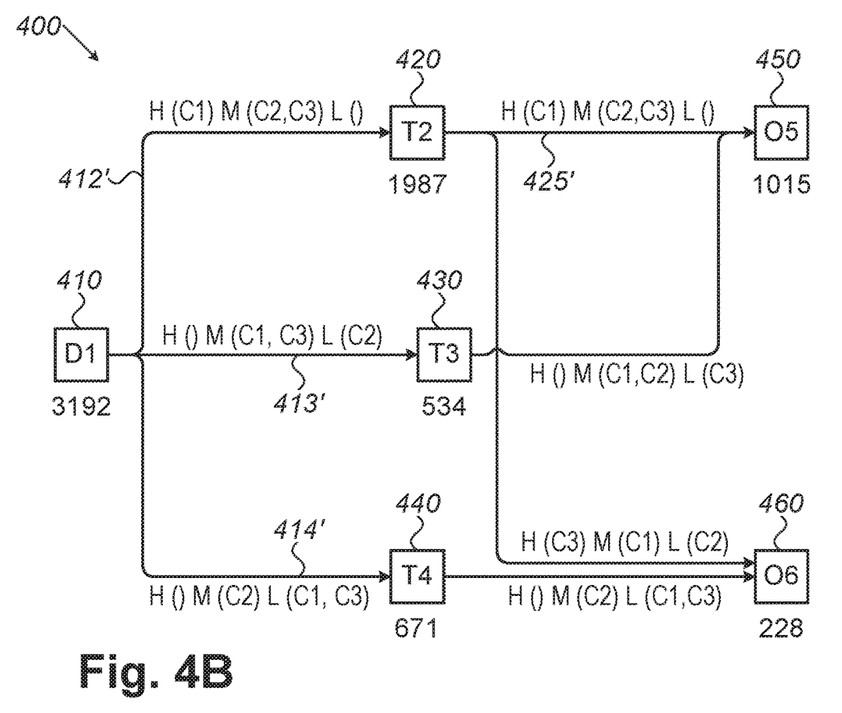
FIG. 4B shows an illustration of a common graph structure, in accordance with some exemplary embodiments of the disclosed subject matter.

Referring now to FIG. 4B showing an illustration of a common graph structure, in accordance with some exemplary embodiments of the disclosed subject matter.

Graph 400 of FIG. 4B displays the relative elative signature trait within a group of all 3 cohorts. For example, Edge 425' representing the edge between T2 420 and O5 450, indicates that the relative traits are High for Cohort1, Medium for Cohort2 and for Cohort3, and that in no case is it labeled with low. This reflects the information shown in Rows 310a, 310b, 310c of FIG. 3.

Similarly, Edge 412' shows that the edge between D1 410 and T2 420 is labeled as high for Cohort1 and as medium for Cohort2 and Cohort3. Edge 413' between D1 410 and T3 430 is labeled with medium for Cohort1 and Cohort3 and with low for Cohort2. Edge 414' between D1 410 and T4 440 is labeled with medium for Cohort2 and with low for Cohort1 and Cohort3.

In some exemplary embodiments, because the labels of Edges 412' and 425' are identical, they may be grouped together in the display and in the analysis.

Figure 5A:
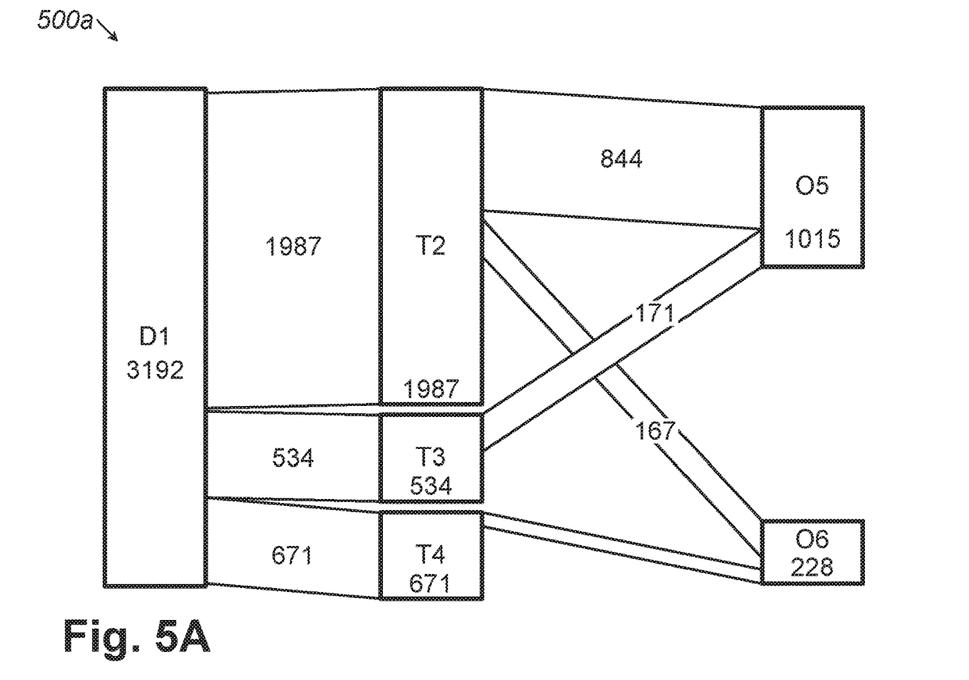
FIGS. 5A-5D show visualizations, in accordance with the disclosed subject matter.

Referring now to FIG. 5A showing a visualization, in accordance with the disclosed subject matter. A Sankey Diagram 500a is displayed showing information regarding all patients in the cohort. Node height and link width may be proportional to the number of patients.

Figure 5B:
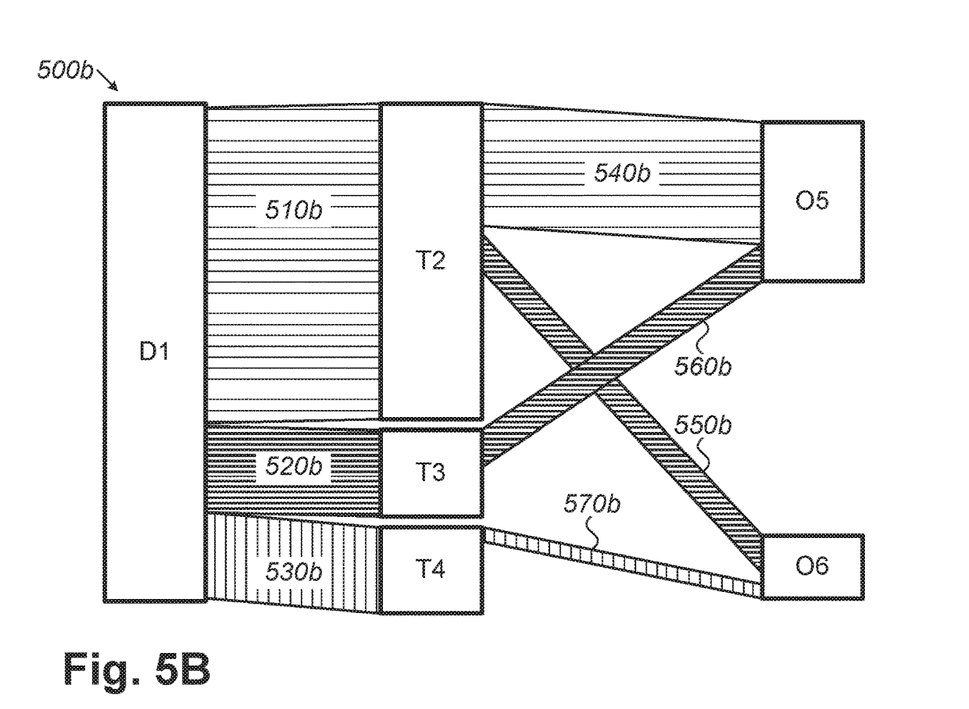

Referring now to FIG. 5B showing a visualization, in accordance with the disclosed subject matter. A Sankey Diagram 500b is displayed and shows the traits of Cohort1 regardless of the other cohorts. Different relative traits may be indicated on the links between nodes, using a visual manner, such as using coloring, pattern, or the like. A first visual marker, such as employed on Links 510b, 540b may indicate high label. A second visual marker, such as employed on Links 520b, 550b, 560b may indicate medium label. A third visual marker, such as employed on Links 530b, 570b, may indicate low label.

As can be appreciated from the illustrative example, Cohort 1 is described as mainly following the trait from to beta blocker treatment (T2) (~60% of the patients), which is most likely to result in hospitalization (O5). Additionally or alternatively, hospitalization (O5) is also the main result of treatment with diuretics (T3).

It is noted that the outcomes in this example indicate bad outcomes (hospitalization or death). Most traits do not result in one of the displayed outcomes, indicated by the area of treatment-nodes is not aligned to one of the paths.

Also visible from Sankey Diagram 500b is that it is least likely that a patient in Cohort1 would be treated with antihypertensive (T4) and would result in death (O6)

Figure 5C:
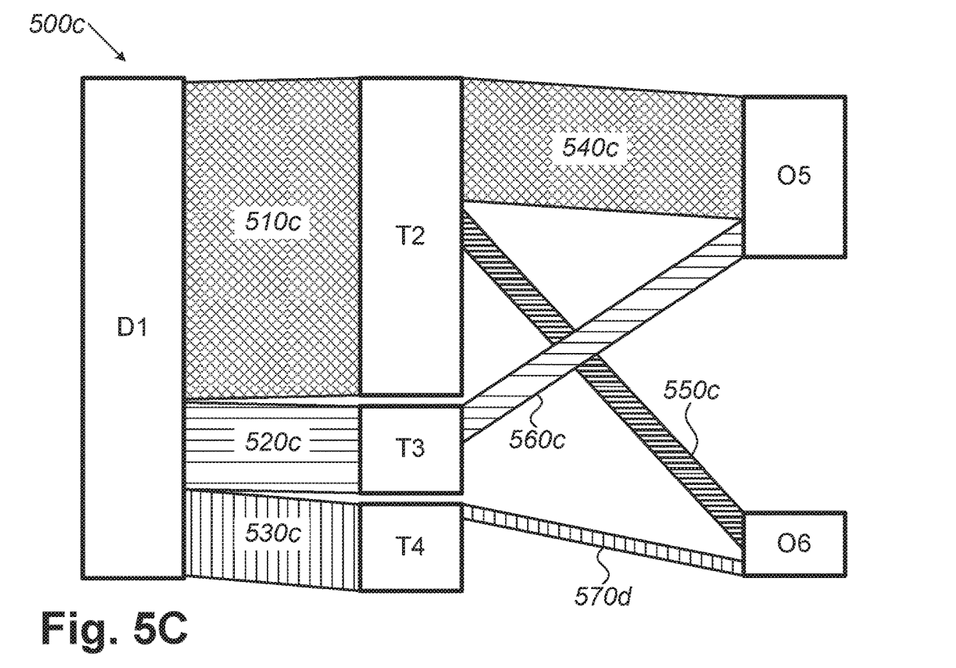

Referring now to FIG. 5C showing a visualization, in accordance with the disclosed subject matter. A Sankey Diagram 500c is displayed and shows the traits of $C_1-(C_2 \cap C_3)$. The diagram may show the patients of Cohort1 without those that are also of both the other cohorts.

The visualization may utilize visual markers to indicate the relative trait of the cohort and also to indicate whether or not the same trait is significant or if it is exhibited in the other cohorts as well. Links 510c, 540c are with significant trait of "high" that is different than the other cohorts. Link 550c is with the trait of "medium" that is different than the other cohorts. However, Links 520c, 560c, 530c, 570c indicate traits that are exhibited in the examined group but are also exhibited by another cohort. For example, from D1 to T3, the label is medium for Cohort1 but also for Cohort3 as is shown in FIG. 3. Links 520*c*, 560*c* represent non-unique medium trait, while Links 530*c*, 570*c* represent non-unique low trait.

As can be appreciated from the Sankey Diagram 500*c*, the trait of CHF diagnosis (D1) to beta blockers treatment (T2) resulting either in hospitalization (O5) or death (O6) is significant for Cohort 1. Other traits, to the other treatments (T3, T4) are not significant for Cohort 1 but occurs also in other cohorts.

In some exemplary embodiments, colors may indicate label, while fill-pattern (e.g. pale fill and outline vs. solid fill) may indicate relative significance of the trait.

Figure 5D:
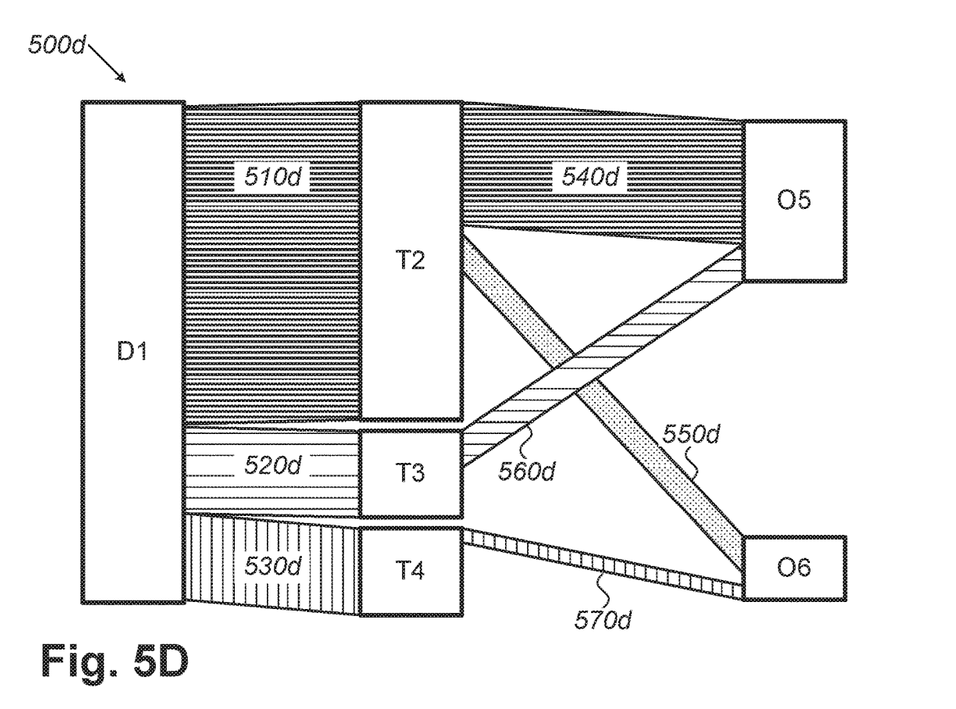

Referring now to FIG. 5D showing a visualization, in accordance with the disclosed subject matter. A Sankey Diagram 500*d* is displayed and shows the traits of $C_1$ OR $C_2$ OR $C_3$. The diagram may show to which cohort, if any, there is a significant signature trait in the relevant link. In some exemplary embodiments, different colors may be used to identify the different cohorts. For example, the color of Links 510*d*, 540*d* may indicate Cohort1. The color of Link 550*d* may indicate Cohort3. The color of Links 530*d*, 570*d* may indicate Cohort2. Additionally or alternatively, the color of Links 520*d*, 560*d* may indicate Cohort1 but may also indicate that it is not a significant trait, such as using a different fill-pattern than that of Link 510*d*.

As can be appreciated, the trait of Cohort 1 is unique to D1 to T2, and also to the result of O5. However, the same treatment resulting in O6 is unique for Cohort 3. Cohort 2 is only identified by the trait to and from T4.

FIG. 5D may indicate for which of the cohorts ($C_1$, $C_2$ or $C_3$) the link has the highest significant signature trait, and whether or not it is unique. For example, Link 510*d* and Link 520*d* may be both color with the same color representing C1 as C1 has a "high" label for Link 510*d* (see 412' of FIG. 4B) and as C1 has a "medium" label for Link 520*d*, where no other cohort has "high" label thereto (see 413' of FIG. 4B). However, as there is no other cohort for which the label is "high" for Link 510*d* such link may be represented by a different fill-pattern than Link 520*d*, for which C3 also has a "medium" label.

It is noted that the disclosed subject matter is provided with the illustrative example of patients and medical data. However, the disclosed subject matter is not limited to such embodiments. The disclosed subject matter may be applied on other types of cohorts and data.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:

for each entity in each cohort of at least two cohorts, extracting a pathway for the each entity, wherein the pathway is extracted from raw data comprising a plurality of events, wherein the pathway is extracted based on events of interest in the plurality of events, wherein the pathway comprises an ordered temporal sequence of events occurring for the each entity;

creating a common graph structure based on the extracted pathways in the at least two cohorts, wherein the common graph structure comprises only one graph structure comprising nodes and edges representing the at least two cohorts, wherein the nodes represent the events of interest, wherein the edges represent subsequent events according to a temporal order, wherein a single edge between a first node and a second node of the nodes indicates an order of occurrences between a first event of the first node and a second event of the second node;

for each cohort of the at least two cohorts, computing at least one relative signature trait for each edge of the common graph structure, wherein said computing the at least one relative signature trait is based on a number of appearances of the each edge in the extracted pathways that are associated with the each cohort, wherein said computing comprises computing, for each cohort, a relative signature trait of the single edge based on a number of times that entities of the each cohort have moved from the first event to the second event according to the order of occurrences;

obtaining a first relationship expression indicating a first selection of a first group of entities from the at least two cohorts, wherein the first relationship expression is configured for providing first indications of first relative signature traits of the first group of entities for each edge of the common graph structure, wherein the first group of entities is defined with respect to the at least two cohorts and comprises at least some entities from different cohorts, wherein each of the at least two cohorts having the at least one relative signature trait computed in said computing, wherein the first relative signature traits are determined based on relative signature traits of the different cohorts that were computed in said computing, wherein the first relationship expression indicates a relation between entities of the at least two cohorts that is to be utilized for computing output labels indicating the first relative signature traits for the edges of the common graph structure;

processing the common graph structure based on the first relationship expression to determine an output label for each edge of the common graph structure, wherein said processing comprises determining the output labels for the edges of the common graph structure based on the relation between the entities of the at least two cohorts and based on the first relative signature traits of the edges of the common graph structure;

displaying a first visualization of the common graph structure, wherein the first visualization comprises a first visual cue indicative of the output labels of each edge of the common graph structure, wherein the first visualization indicates the first relative signature traits;

obtaining a second relationship expression indicating a second selection of a second group of entities from the at least two cohorts that is different from the first group of entities, wherein the second relationship expression is configured for providing second indications of second relative signature traits of the second group of entities for each edge of the common graph structure, wherein the second relative signature traits are determined based on relative signature traits of one or more cohorts that comprise the second group of entities;

processing the common graph structure based on the second relationship expression to determine second output labels for each edge of the common graph structure, wherein said processing comprises determining the second output labels for the edges of the common graph structure based on the second relative signature traits of the edges of the common graph structure; and displaying a second visualization of the common graph structure, wherein the second visualization comprises a second visual cue indicative of the second output labels of each edge, wherein the second visualization indicates the second relative signature traits.

2. The method of claim 1, wherein the first visualization comprises an aggregative edge, wherein the aggregative edge represents a sub-path comprising edges having a same output label, wherein the aggregative edge is associated with the same output label.

3. The method of claim 2, wherein in response to user interaction with the aggregative edge, displaying the edges of the sub-path individually.

4. The method of claim 1 further comprising:
obtaining the second relationship expression with respect to the at least two cohorts, wherein the second relationship expression indicates a second relation between entities of the at least two cohorts that is to be utilized for computing the second output labels for the edges of the common graph structure;
processing the common graph structure based on the second relationship expression to determine a second output label for each edge, wherein said processing comprises determining the second output labels for the edges of the common graph structure based on the second relation between the entities of the at least two cohorts and based on the second relative signature traits of the edges of the common graph structure; and
displaying the second visualization of the common graph structure, wherein the second visualization comprises the second visual cue indicative of the second output label of each edge,
whereby said processing the common graph structure based on the first relationship expression and said processing the common graph structure based on the second relationship expression are performed based on the common graph structure and the at least one relative signature trait without additional pre-processing, wherein the common graph structure and the at least one relative signature trait of each edge are not recalculated.

5. The method of claim 1, wherein the first relationship expression is provided using set algebra.

6. The method of claim 1, wherein said processing the common graph structure based on the first relationship expression is performed based on the at least one relative signature trait of each edge and without computing traits based on pathways associated with the first group represented by the first relationship expression.

7. A non-transitory computer readable medium retaining program instructions, which program instructions when read by a processor, cause the processor to perform:
for each entity in each cohort of at least two cohorts, extracting a pathway for the each entity, wherein the pathway is extracted from raw data comprising a plurality of events, wherein the pathway is extracted based on events of interest in the plurality of events, wherein the pathway comprises an ordered temporal sequence of events occurring for the each entity;
creating a common graph structure based on the extracted pathways in the at least two cohorts, wherein the common graph structure comprises only one graph structure comprising nodes and edges representing the at least two cohorts, wherein the nodes represent the events of interest, wherein the edges represent subsequent events according to a temporal order, wherein a single edge between a first node and a second node of the nodes indicates an order of occurrences between a first event of the first node and a second event of the second node;
for each cohort of the at least two cohorts, computing at least one relative signature trait for each edge of the common graph structure, wherein said computing the at least one relative signature trait is based on a number of appearances of the each edge in the extracted pathways that are associated with the each cohort, wherein said computing comprises computing, for each cohort, a relative signature trait of the single edge based on a number of times that entities of the each cohort have moved from the first event to the second event according to the order of occurrences;
obtaining a first relationship expression indicating a first selection of a first group of entities from the at least two cohorts, wherein the first relationship expression is configured for providing first indications of first relative signature traits of the first group of entities for each edge of the common graph structure, wherein the first group of entities is defined with respect to the at least two cohorts and comprises at least some entities from different cohorts, wherein each of the at least two cohorts having the at least one relative signature trait computed in said computing, wherein the first relative signature traits are determined based on relative signature traits of the different cohorts that were computed in said computing, wherein the first relationship expression indicates a relation between entities of the at least two cohorts that is to be utilized for computing output labels indicating the first relative signature traits for the edges of the common graph structure;
processing the common graph structure based on the first relationship expression to determine an output label for each edge of the common graph structure, wherein said processing comprises determining the output labels for the edges of the common graph structure based on the relation between the entities of the at least two cohorts and based on the first relative signature traits of the edges of the common graph structure;
displaying a first visualization of the common graph structure, wherein the first visualization comprises a first visual cue indicative of the output labels of each edge of the common graph structure, wherein the first visualization indicates the first relative signature traits;
obtaining a second relationship expression indicating a second selection of a second group of entities from the at least two cohorts that is different from the first group of entities, wherein the second relationship expression is configured for providing second indications of second relative signature traits of the second group of entities for each edge of the common graph structure, wherein the second relative signature traits are determined based on relative signature traits of one or more cohorts that comprise the second group of entities;

processing the common graph structure based on the second relationship expression to determine second output labels for each edge of the common graph structure, wherein said processing comprises determining the second output labels for the edges of the common graph structure based on the second relative signature traits of the edges of the common graph structure; and displaying a second visualization of the common graph structure, wherein the second visualization comprises a second visual cue indicative of the second output labels of each edge, wherein the second visualization indicates the second relative signature traits.

8. The non-transitory computer readable medium of claim 7, wherein the first visualization comprises an aggregative edge, wherein the aggregative edge represents a sub-path comprising edges having a same output label, wherein the aggregative edge is associated with the same output label.

9. The non-transitory computer readable medium of claim 8, wherein in response to user interaction with the aggregative edge, displaying the edges of the sub-path individually.

10. The non-transitory computer readable medium of claim 7, wherein said program instructions when read by the processor, cause the processor to perform:

obtaining the second relationship expression with respect to the at least two cohorts, wherein the second relationship expression indicates a second relation between entities of the at least two cohorts that is to be utilized for computing the second output labels for the edges of the common graph structure;

processing the common graph structure based on the second relationship expression to determine a second output label for each edge, wherein said processing comprises determining the second output labels for the edges of the common graph structure based on the second relation between the entities of the at least two cohorts and based on the second relative signature traits of the edges of the common graph structure; and displaying the second visualization of the common graph structure, wherein the second visualization comprises the second visual cue indicative of the second output label of each edge, whereby said processing the common graph structure based on the relationship expression and said processing the common graph structure based on the second relationship expression are performed based on the common graph structure and the at least one relative signature traits without additional pre-processing, wherein the common graph structure and the at least one relative signature trait of each edge are not recalculated.

11. The non-transitory computer readable medium of claim 7, wherein the first relationship expression is provided using set algebra.

12. The non-transitory computer readable medium of claim 7, wherein said processing the common graph structure based on the first relationship expression is performed based on the at least one relative signature trait of each edge and without computing traits based on pathways associated with the first group represented by the first relationship expression.

13. An apparatus comprising a processor and memory, wherein the processor is configured to perform:

for each entity in each cohort of at least two cohorts, extracting a pathway for the each entity, wherein the pathway is extracted from raw data comprising a plurality of events, wherein the pathway is extracted based on events of interest in the plurality of events, wherein the pathway comprises an ordered temporal sequence of events occurring for the each entity;

creating a common graph structure based on the extracted pathways in the at least two cohorts, wherein the common graph structure comprises only one graph structure comprising nodes and edges representing the at least two cohorts, wherein the nodes represent the events of interest, wherein the edges represent subsequent events according to a temporal order, wherein a single edge between a first node and a second node of the nodes indicates an order of occurrences between a first event of the first node and a second event of the second node;

for each cohort of the at least two cohorts, computing at least one relative signature trait for each edge of the common graph structure, wherein said computing the at least one relative signature trait is based on a number of appearances of the each edge in the extracted pathways that are associated with the each cohort, wherein said computing comprises computing, for each cohort, a relative signature trait of the single edge based on a number of times that entities of the each cohort have moved from the first event to the second event according to the order of occurrences;

obtaining a first relationship expression indicating a first selection of a first group of entities from the at least two cohorts, wherein the first relationship expression is configured for providing first indications of first relative signature traits of the first group of entities for each edge of the common graph structure, wherein the first group of entities is defined with respect to the at least two cohorts and comprises at least some entities from different cohorts, wherein each of the at least two cohorts having the at least one relative signature trait computed in said computing, wherein the first relative signature traits are determined based on relative signature traits of the different cohorts that were computed in said computing, wherein the first relationship expression indicates a relation between entities of the at least two cohorts that is to be utilized for computing output labels indicating the first relative signature traits for the edges of the common graph structure;

processing the common graph structure based on the first relationship expression to determine an output label for each edge of the common graph structure, wherein said processing comprises determining the output labels for the edges of the common graph structure based on the relation between the entities of the at least two cohorts and based on the first relative signature traits of the edges of the common graph structure;

displaying a first visualization of the common graph structure, wherein the first visualization comprises a first visual cue indicative of the output labels of each edge of the common graph structure, wherein the first visualization indicates the first relative signature traits;

obtaining a second relationship expression indicating a second selection of a second group of entities from the at least two cohorts that is different from the first group of entities, wherein the second relationship expression is configured for providing second indications of second relative signature traits of the second group of entities for each edge of the common graph structure, wherein the second relative signature traits are determined based on relative signature traits of one or more cohorts that comprise the second group of entities;

processing the common graph structure based on the second relationship expression to determine second output labels for each edge of the common graph structure, wherein said processing comprises determining the second output labels for the edges of the common graph structure based on the second relative signature traits of the edges of the common graph structure; and displaying a second visualization of the common graph structure, wherein the second visualization comprises a second visual cue indicative of the second output labels of each edge, wherein the second visualization indicates the second relative signature traits; and wherein said memory is configured to retain the first and second relative signature traits, the common graph structure and the first and second output labels.

14. The apparatus of claim 13, wherein the first visualization comprises an aggregative edge, wherein the aggregative edge represents a sub-path comprising edges having a same output label, wherein the aggregative edge is associated with the same output label.

15. The apparatus of claim 14, wherein in response to user interaction with the aggregative edge, displaying the edges of the sub-path individually.

16. The apparatus of claim 13, wherein said processor is further adapted to perform:

obtaining the second relationship expression with respect to the at least two cohorts, wherein the second relationship expression indicates a second relation between entities of the at least two cohorts that is to be utilized for computing the second output labels for the edges of the common graph structure;

processing the common graph structure based on the second relationship expression to determine a second output label for each edge, wherein said processing comprises determining the second output labels for the edges of the common graph structure based on the second relation between the entities of the at least two cohorts and based on the second relative signature traits of the edges of the common graph structure; and displaying the second visualization of the common graph structure, wherein the second visualization comprises the second visual cue indicative of the second output label of each edge, whereby said processing the common graph structure based on the relationship expression and said processing the common graph structure based on the second relationship expression are performed based on the common graph structure and the at least one relative signature traits without additional pre-processing, wherein the common graph structure and the at least one relative signature trait of each edge are not recalculated.

17. The apparatus of claim 13, wherein the first relationship expression is provided using set algebra.

18. The apparatus of claim 13, wherein said processing the common graph structure based on the first relationship expression is performed based on the at least one relative signature trait of each edge and without computing traits based on pathways associated with the first group represented by the first relationship expression.

* * * * *